United States Patent [19]

Wadsworth et al.

[11] Patent Number: 5,470,859
[45] Date of Patent: Nov. 28, 1995

[54] AZABICYCLIC COMPOUNDS WITH MUSCARINIC ACTIVITY USEFUL FOR TREATING DEMENTIA

[75] Inventors: Harry J. Wadsworth; Paul A. Wyman; Steven Dabbs; Sarah M. Jenkins, all of Harlow, England

[73] Assignee: Beecham Group p.l.c., Middlesex, England

[21] Appl. No.: 561,974

[22] Filed: Aug. 2, 1990

[30] Foreign Application Priority Data

Aug. 5, 1989 [GB] United Kingdom ............ 8917957

[51] Int. Cl.$^6$ .................... C07D 453/02; A61K 31/435
[52] U.S. Cl. .................... 514/299; 514/305; 546/112; 546/133
[58] Field of Search .................... 546/133, 112; 514/305, 299

[56] References Cited

FOREIGN PATENT DOCUMENTS

| | | |
|---|---|---|
| 0239309 | 9/1987 | United Kingdom . |
| 0261763 | 3/1988 | United Kingdom . |
| 0287356 | 10/1988 | United Kingdom . |
| 0307141 | 3/1989 | United Kingdom . |
| 0307142 | 3/1989 | United Kingdom . |
| 0316718 | 5/1989 | United Kingdom . |
| 0322182 | 6/1989 | United Kingdom . |
| 0323864 | 7/1989 | United Kingdom . |
| 0339834 | 11/1989 | United Kingdom . |
| 0363085 | 4/1990 | United Kingdom . |
| 0366304 | 5/1990 | United Kingdom . |
| 0375450 | 6/1990 | United Kingdom . |
| 0398617 | 11/1990 | United Kingdom . |
| 0398616 | 11/1990 | United Kingdom . |
| 0402056 | 12/1990 | United Kingdom . |

OTHER PUBLICATIONS

Journal of Organic Chemistry vol. 31, No. 9, 1966 pp. 2957–2962; F. I. Carroll et al.
Journal of Organic Chemistry vol. 34, No. 11, 1969 pp. 3674–3676, D. O. Spry et al.

*Primary Examiner*—Johann Richter
*Assistant Examiner*—Catherine Scalzo
*Attorney, Agent, or Firm*—Hopgood, Calimafde, Kalil & Judlowe

[57] ABSTRACT

A pharmaceutical composition useful to treating dementia which comprises a compound of formula (I) or a pharmaceutically acceptable salt thereof:

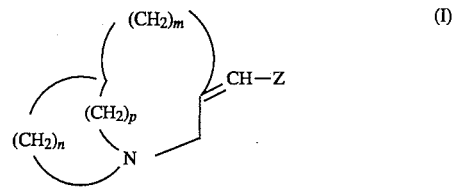

in which p is 1 and either m is 0 and n is 2 or 3 or m is 1 and n is 2, or p is 2, m is 0 and n is 2, and Z is a heterocyclic group

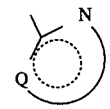

in which Q represents a 3-membered divalent residue completing a 5-membered aromatic ring and comprises one or two heteroatoms selected from oxygen, nitrogen and sulphur, or three nitrogen atoms, any amino nitrogen being substituted by a $C_{1-2}$ alkyl, cyclopropyl or propargyl group, and any ring carbon atom being optionally substituted by a group $R_1$; or a group

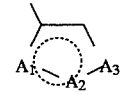

which $A_1$, $A_2$ and $A_3$ complete a 5-membered aromatic ring and $A_1$ is oxygen or sulphur, one of $A_2$ and $A_3$ is $CR_2$ and the other is nitrogen or $CR_3$, or $A_2$ is oxygen or sulphur, one of $A_1$ and $A_3$ is $CR_2$ and the other is $CR_3$; and $R_1$, $R_2$ and $R_3$ are independently selected from hydrogen, halogen, $N(R_4)_2$, $C_{2-3}$ alkenyl, $C_{2-3}$ alkynyl or $C_{1-2}$ alkyl optionally substituted with one, two or three fluorine atoms, in which $R_4$ is hydrogen or methyl, and a pharmaceutically acceptable carrier.

9 Claims, No Drawings

AZABICYCLIC COMPOUNDS WITH MUSCARINIC ACTIVITY USEFUL FOR TREATING DEMENTIA

This invention relates to compounds having pharmaceutical activity, to a process for their preparation and their use as pharmaceuticals.

EP-A-0261763 and EP-A-0322182 disclose certain non-aromatic 1-azabicyclic ring systems substituted at the 3-position by certain 5-membered aromatic heterocycles. EP-A-0363085 (published 11.04.90) discloses certain non-aromatic 1-azabicyclic ring systems substituted at the 3-position by methyl itself substituted by certain 5-membered aromatic heterocycles.

EP-A-0239309, EP-A-0307141 and EP-A-0307142 disclose certain substituted oxadiazoles, thiadiazoles, 1,3-oxazoles and 1,3-thiazoles for the treatment of neurological and mental illness whose clinical manifestations are due to involvement of cholinergic neurones.

A class of compounds has been discovered which enhance acetylcholine function via an action at muscarinic receptors within the central nervous system and are therefore of potential use in the treatment and/or prophylaxis of dementia in mammals.

According to the present invention, there is provided a pharmaceutical composition which comprises compound of formula (I) or a pharmaceutically acceptable salt thereof:

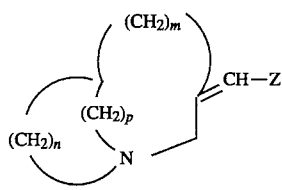

in which p is 1 and either m is 0 and n is 2 or 3 or m is 1 and n is 2, or p is 2, m is 0 and n is 2, and Z is a heterocyclic group

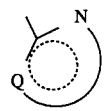

in which Q represents a 3-membered divalent residue completing a 5-membered aromatic ring and comprises one or two heteroatoms selected from oxygen, nitrogen and sulphur, or three nitrogen atoms, any amino nitrogen being substituted by a $C_{1-2}$ alkyl, cyclopropyl or propargyl group, and any ring carbon atom being optionally substituted by a group $R_1$; or a group

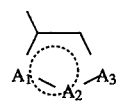

in which $A_1$, $A_2$ and $A_3$ complete a 5-membered aromatic ring and $A_1$ is oxygen or sulphur, one of $A_2$ and $A_3$ is $CR_2$ and the other is nitrogen or $CR_3$, or $A_2$ is oxygen or sulphur, one of $A_1$ and $A_3$ is $CR_2$ and the other is $CR_3$; and $R_1$, $R_2$ and $R_3$ are independently selected from hydrogen, halogen, $N(R_4)_2$, $C_{2-3}$ alkenyl, $C_{2-3}$ alkynyl or $C_{1-2}$ alkyl optionally substituted with one, two or three fluorine atoms, in which $R_4$ is hydrogen or methyl, and a pharmaceutically acceptable carrier.

The invention also provides novel compounds within formula (I) or a pharmaceutically acceptable salts thereof excluding Z 3-([1,3-thiazol-2-yl]methylene)-1-azabicyclo [2.2.2]octane. Such compounds are hereinafter referred to as compounds of formula (Ia).

There is a preferred sub-group of compounds of formula (I) in which p is 1.

Compounds of formula (I) are capable of existing in a number of stereoisomeric forms including geometrical isomers in both the E- and Z- configurations. The invention extends to each of these configurations, and to mixtures thereof. Different stereoisomeric forms may be separated one from the other by usual methods for example using crystallisation techniques. It is preferred that compounds of formula (I) exist in the Z-configuration.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

Examples of [p,n,m] include [1,2,0], [2,2,0] and [1,2,1]

p is preferably 1.

n is preferably 2.

m is preferably 0.

5-Membered aromatic heterocycles within the definition of variable Z include oxadiazole such as 1,2,4-oxadiazol-5-yl, 1,2,4-oxadiazol-3-yl and 1,3,4-oxadiazol-2-yl, oxazole such as 1,3-oxazol-2-yl, 1,3-oxazol-4-yl 1,3-oxazol-5-yl, 1,2-oxazol-3-yl and 1,2-oxazol-5-yl, thiadiazole such as 1,2,4-thiadiazol-5-yl and 1,3,4-thiadiazol-2-yl, thiazole such as 1,3-thiazol-2-yl, 1,3-thiazol-5-yl and 1,2-thiazol-5-yl, furan such as furan-2-yl and furan-3-yl, triazole such as 1-alkyl-, 2-alkyl-, or 3-alkyl-1,2,3-triazol-4-yl and 1,2,4-triazol-3-yl including 1-alkyl-1,2,4-triazol-3-yl, 1-alkyltetrazol- 5-yl and 2-alkyl-tetrazol-5-yl, where 'alkyl' signifies a $C_{1-2}$alkyl, cyclopropyl or propargyl group.

Values for $R_1$, $R_2$ and $R_3$ include hydrogen, methyl, ethyl, $NH_2$ and $CH_2F$, preferably hydrogen, methyl and $NH_2$.

It will be appreciated that the range of values for $R_1$, $R_2$ and $R_3$ will be limited by the preparative constraints and/or stability of the group Z. For example, an oxazole ring will tolerate a 2-amino substituent whereas 2-amino-furans are unstable. Conversely, 2-halo-furans are stable whereas 2-halooxazoles are very labile compounds. Where z is a tri- or tetrazole group, the amino nitrogen must be substituted, preferably γ to the position of the methylene-azabicyclic moiety.

Examples of Z include 3-amino-1,2,4-oxadiazol-5-yl, 3-methyl-1,2,4-oxadiazol-5-yl, 1,3-oxazol-2-yl, 1,3-thiazol-2-yl, 5-methyl-1,3-oxazol-2-yl and 1,3-oxazol-5-yl.

The invention also provides a process for the preparation of a compound of formula (I), or a pharmaceutically acceptable salt thereof, which process comprises (a) cyclising a compound of formula (II):

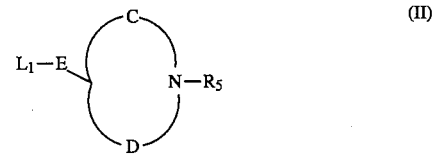

where $R_5$ is hydrogen or an N-protecting group, and either C is one, D is another and E is the remainder of $-(CH_2)_n-$, $-(CH_2)_p-$ and $-(CH_2)_m-C(=CH-Z)-CH_2-$ or groups convertible thereto and $L_1$ is a leaving group; or C is one and E is the other of —(CH₂)ₙ— and —(CH₂)ₚ— or groups convertible thereto and D represents —(CH₂)ₘ—CHA'—CH₂— where A' and L₁ together represent —COO—, and thereafter, optionally or as necessary and in any appropriate order, converting C, D and E to —(CH₂)ₙ—, —(CH₂)ₚ— and —(CH₂)ₘ—C(=CH—Z)—CH₂—, removing any R₅ protecting group, optionally interconverting Z and/or forming a pharmaceutically acceptable salt; or (b) cyclising a compound of formula (III):

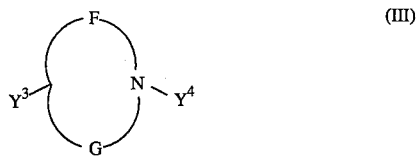

(III)

where F is one and G is the other of —(CH₂)ₙ— and —(CH₂)ₚ— or groups convertible thereto, and one of Y³ and Y⁴ is —(CH₂ᵤ—K and the other is —(CH₂)ᵥW or —(CH₂)ᵥL₂ where K and W are electron withdrawing groups, L₂ is a leaving group, u is 1 or 2 and v is 0 or 1, with the proviso that when Y⁴ is —(CH₂)ᵥW, v is 1, and Y⁴ is not —(CH₂)ᵥL₂, u and v being such that the desired compound of formula (I) is obtained, and thereafter, optionally or as necessary and in any appropriate order, where one of Y³ and Y⁴ is —(CH₂)ᵥW, 1, hydrolysing and decarboxylating the cyclisation product and converting the C=O group to C=CHZ, where Y³ is —(CH₂)ᵥL₂, converting the CHK group to C=CHZ, converting F and G to —(CH₂)ₙ— and —(CH₂)ₚ— as appropriate, interconverting Z and/or forming a pharmaceutically acceptable salt.

The deprotection, conversion and interconversion steps may be carried out in any appropriate order.

In process variant (a), examples of leaving groups L₁ include halo such as chloro and hydroxy. Examples of groups convertible to —(CH₂)ₘ—C(=CH—Z)CH₂— include —(CH₂)ₘCOCH₂— and —(CH₂)ₘCHA'CH₂—. In process variant (b), examples of L₂ include those given for L₁ or C₁₋₄ alkoxy such as ethoxy. Examples of electron withdrawing groups K and w include C₁₋₄ alkoxycarbonyl and cyano. In the group —(CH₂)ₘCHA'—CH₂—, examples of A' include hydroxy, cyano and formyl.

In process variant (a), where L₁ is hydroxy and D is —(CH₂))ₘCHOH—CH₂—, the cyclisation of compounds of formula (III) may be carried out by pyrolysis, by the method of D. O. Spry and H. S. Aaron, J. Org. Chem., 1969, 34, 3674, to yield a compound where A' is hydroxy.

An A' hydroxy group may be oxidised to a carbonyl group by treatment with chromic acid or using dimethyl sulphoxide and dicyclohexyl carbodiimide.

Where E is —(CH₂)ₘCO—CH₂—, the cyclisation may be carried out under basic conditions where R₅ is benzyl (F. I. Carrol, A. M. Ferguson, and J. B. Lewis, J. Org. Chem. 31, 2957, 1966).

Where L₁ and A' together represent —COO—, the cyclisation is a rearrangement reaction which can be carried out under acid conditions in a polar solvent, such as hydrogen bromide in ethanol, at ambient temperature followed by treatment with base such as aqueous potassium carbonate, to yield a compound where A' is a carboxy ester group. It is preferred to protect the nitrogen atom with an R₅ N-protecting group such as benzyl or substituted benzyl, which may be subsequently removed by hydrogenation over a suitable catalyst such as pd/C.

In process variant (b), where Y³ and Y⁴ both contain carboxy ester groups the cyclisation of compounds of formula (III) is a Dieckmann reaction which is catalysed by a base such as potassium t-butoxide at elevated temperature in a solvent such as toluene.

The resulting β-keto ester is hydrolysed and decarboxylated under conventional conditions such as heating at reflux in dilute hydrochloric acid.

In process variant (b) where Y³ and Y⁴ both contain cyano groups the cyclisation is a Thorpe reaction which is catalysed by a base such as potassium t-butoxide at elevated temperature in a solvent such as toluene.

The resulting β-keto nitrile is hydrolysed and decarboxylated under conventional conditions such as heating at reflux in dilute hydrochloric acid.

Where Y³ is —(CH₂)ᵥL₂, the cyclisation may be carried out as described in EP-0094742 under basic conditions such as sodium hydride and potassium t-butoxide, in an inert polar solvent such as dimethylformamide.

Conversions of groups A' and K and of the carbonyl group from process variant (b), and interconversions of Z, may be carried out conventionally, see for example standard text books on heterocyclic chemistry such as 'Comprehensive Heterocyclic Chemistry', A. R. Katritzky and C. W. Rees, Pergamon, 1984.

A carbonyl group may be reacted with tosylmethyl isocyanide to yield a compound where A' is cyano, or with methoxymethyl triphenyl phosphonium chloride and potassium t-butoxide in dimethyl formamide followed by aqueous acid hydrolysis of the enol ether to yield a compound where A' is formyl.

Alternatively, the carbonyl group may be reduced to an A' hydroxy group with a suitable reducing agent such as sodium borohydride in ethanol at ambient temperature, or sodium in ethanol at elevated temperature, such as the boiling point of the solvent, under an inert atmosphere such as nitrogen.

An A' hydroxy group may be converted to cyano by first converting it to a good leaving group such as mesyloxy or tosyloxy and then displacing it with cyanide ion.

An A' formyl group may be obtained by conventional reduction of an A' or K alkoxycarbonyl group with a reducing agent such as diisobutylaluminium hydride in an inert solvent such as toluene at low temperature, or, more preferably hydrolysis with acid, followed by conversion to the acid chloride by treatment with thionyl chloride and reaction with O-N-methylated dimethyl hydroxylamine hydrochloride in the presence of pyridine in a suitable solvent such as dichloromethane to give the O-N-dimethyl hydroxamic acid. Reduction with diisobutyl aluminium hydride under similar conditions as above yields the required formyl group.

An A' formyl group may be converted to CH₂ CN by treatment with p-toluenesulphonylmethyl isocyanide under basic conditions at depressed temperature.

A Z 2- or 3-furyl or 1,3-thiazol-2-yl group may be obtained by treatment of an A' formyl group with the anion of the heterocycle. In the case of 2- or 3-furyl, the lithium salt of furan is generated by treatment of furan with lithium diisopropylamide or a furan derivative such as 2- or 3-bromofuran with n-butyl lithium in an inert solvent such as diethylether at reduced temperature, followed by dehydration of the resulting secondary alcohol either with a Lewis acid such as tin (Iv) chloride to afford the vinyl furan or with a suitable dehydrating agent such as methanesulphonyl chloride and pyridine. In the case of 1,3-thiazol-2-yl, 2-trimethylsilyl-1,3-thiazole activated with fluoride ion is used and the resulting secondary alcohol is dehydrated under the conditions described above.

In a preferred aspect, the process comprises the reaction of the compound of formula (IV):

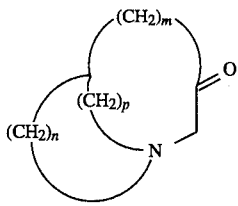
(IV)

with a phosphorus ylide of formula (V) or (VI):

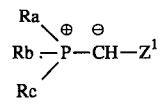
(V)

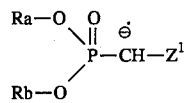
(VI)

in which Ra, Rb and Rc are independently $C_{1-6}$ alkyl, aryl or aralkyl and $Z^1$ is alkoxy or a carboxylic acid, or ester or amide derivative thereof to give a compound of formula (VII):

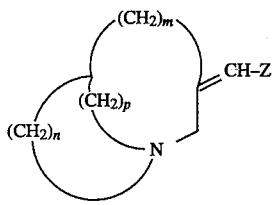
(VII)

in which $Z^1$ is as defined for formulae (V) and (VI); and thereafter converting $Z^1$ to Z, optionally interconverting Z and/or forming a pharmaceutically acceptable salt.

The reaction of a compound of formula (IV) with a phosphorus ylide of formula (V) or (VI) which is equivalent to the conversion of a ketone to an olefin is known as a wittig Reaction and may be carried out under conditions generally used for such reactions. Preferably a compound of formula (IV) is reacted with a compound of formula (VI) in which Ra and Rb are each $C_{1-6}$ alkyl, for example ethyl, and $Z^1$ is an ester function, for example ethoxycarbonyl.

Where it is required that Z' in the compound of formula (VII) is an amide derivative, it may be convenient to amide derivative or alternatively to use a compound of formula (V) or (VI) in which $Z^1$ is an ester derivative and convert $Z^1$ in the resulting compound of formula (VII) from ester to amide, for example by treatment with ammonia.

Certain specific Z groups may be obtained by alternative routes. Thus, a Z 1,2,4-thiadiazol-5-yl group may be introduced by reaction of a ketone of formula (IV) with a compound:

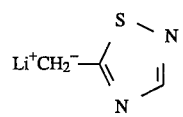

at low temperature under anhydrous conditions in tetrahydrofuran, followed by dehydration of the resulting alcohol.

Conversion of $Z^1$ to a heterocyclic group Z, as defined for formula (I), may be carried out using procedures as described in, for example standard text books on heterocyclic chemistry such as 'Comprehensive Heterocyclic Chemistry', A. R. Katritzky and C. W. Rees, Pergamon, 1984.

The $Z^1$ group is first converted, as necessary, to a suitable starting group Z' for the chosen conversion reaction to give the required group Z.

A Z' carboxy group may be obtained by conventional de-esterification of a $Z^1$ alkoxycarbonyl group.

A Z' chlorocarbonyl group may be obtained by treatment of a Z' carboxy group with thionyl chloride at elevated temperature.

A Z' aminocarbonyl group may be obtained by treatment of a Z' chlorocarbonyl group with ammonia.

A Z' cyano group may be obtained by treatment of a $Z^1$ aminocarbonyl group with a dehydrating agent such as phosphorus pentoxide in toluene or trifluoracetic acid anhydride in tetrahydrofuran and pyridine.

A Z' $CH_3CO$— group may be obtained by treatment of a LiOOC group with methyl lithium, the LiOOC group being obtained by hydrolysis of a Z' alkoxycarbonyl group with lithium hydroxide in water. Alternatively, a Z' $CH_3CO$— group may be obtained by reaction of a Z' chlorocarbonyl group with N,O-dimethylhydroxylamine and treatment with methyl lithium or methyl Grignard reagent.

A Z' bromomethylcarbonyl group may be obtained by treatment of a Z' $COCH_3$ group either with bromine in a suitable solvent such as methanol, the nitrogen of the azabicycle being protected as the hydrochloride or hydrobromide salt, or with lithium diisopropylamide and trimethylsilyl chloride at low temperature followed by N-bromosuccinimide in tetrahydrofuran at low temperature. Alternatively, a Z' —COCl group may be converted to a —$COCH_2Br$ group by treatment with diazomethane in ether at low temperature followed by hydrogen bromide in acetic acid at ambient temperature.

A Z' $CH_2N{\equiv}C$ group may be obtained from a formamidomethyl group by treatment with phosgene and triethylamine. The formamidomethyl group may in turn be obtained from the aminomethyl group by reaction with an ester of formic acid such as ethyl formate. The aminomethyl group may be obtained by reduction of the aminocarbonyl group with lithium aluminium hydride.

A Z' formyl group may be obtained from a $Z^1$ alkoxycarbonyl group as described above for the corresponding conversion of an A' alkoxycarbonyl group.

When Z represents a 1,2,3-triazol-4-yl group, a Z' formyl group may be treated with triphenyl phosphine, carbon tetrabromide and zinc in an inert solvent such as dichloromethane at ambient temperature to provide a 2,2-dibromoethenyl group which may be eliminated with n-butyl lithium in hexane to give an ethynyl group. Treatment of the latter with azidotrimethyl silane in an inert solvent such as tetrahydrofuran at elevated temperature followed by lower alcohol at ambient temperature yields the unsubstituted 1,2,3-triazol-4-yl group which is alkylated as required. A 2-alkyl group may be introduced by treatment with the corresponding diazoalkane in ether at ambient temperature.

Compounds of formula (I) in which Z represents a 1-alkyl or 3-alkyl-1,2,3-triazol-4-yl group may be obtained as minor products in the preparation of the corresponding 2-alkyl-1, 2,3-triazol-4-yl compounds and separated chromatographically.

When Z represents a 2-alkyltetrazol-5-yl group, a Z' cyano group may be treated with azidotrimethyl silane in an inert solvent such as tetrahydrofuran at elevated temperature to yield a 2-trimethylsilyl-2H-tetrazol-5 -yl group. Treatment of the latter with methanol effects deprotection of the amino nitrogen which may then be alkylated as described above.

Compounds of formula (I) in which Z represents a 1-alkyltetrazol-5-yl group may be obtained as a minor product in the preparation of the corresponding 2-alkyltetrazol-5-yl compound and separated chromatographically.

When Z represents a 1,2,4-triazol-3-yl group a Z' cyano group may be treated with dry ethanol saturated with hydrogen chloride gas to give an imidate. This may be treated with an alkyl hydrazine to form the corresponding amidrazone. Treatment of this with anhydrous formic acid or triethyl orthoformate will give the required 1-alkyl-1,2,4-triazol-3-yl group.

When Z represents 3-substituted-1,2,4-oxadiazol-5-yl, a Z' chlorocarbonyl or Z' carboxy ester group may be reacted with an appropriate amide oxime, at elevated temperature in an inert, polar solvent such as chloroform, and the resulting substitution product cyclised at elevated temperature in a suitable solvent such as toluene or xylene.

For example, when Z represents 3-methyl-1,2,4 -oxadiazol-5-yl, a Z' chlorocarbonyl group may be reacted with acetamide oxime, at elevated temperature in an inert, polar solvent such as chloroform, and the resulting substitution product cyclised at elevated temperature in a suitable solvent such as toluene or xylene. Alternatively, reaction of a Z' aminocarbonyl group with an acetal of N,,N-dimethylacetamide such as the dimethyl or diethyl acetal at elevated temperature yields an acyl amidine group —CON=C(CH$_3$)N(CH$_3$)$_2$ which may then be reacted with hydroxylamine, in the presence of acid, such as acetic acid, which may also function as the solvent. The reaction may be carried out at ambient temperature, the N-hydroxy acyl amidine intermediate optionally isolated and then cyclised at elevated temperature, or alternatively in a single step at elevated temperature. When Z represents 3-amino-1,2,4-oxadiazol-5-yl, a Z' chlorocarbonyl or Z' carboxy ester group may be reacted with a hydroxy guanidine derivative under basic conditions.

When Z represents 3-(H or methyl)-1,2,4-thiadiazol-5-yl, a Z' aminocarbonyl group may be converted into an aminothiocarbonyl group using phosphorus pentasulphide or Lawesson's reagent (S. Scheibye, B. S. Pederson and J. O. Lawesson, Bull. Soc. Chim. Belg., 1978, 87 (3), 229). The aminothiocarbonyl may be converted into a thioacyl amidine group and cyclised as described above for the 1,2,4-oxadiazole group.

When Z represents b 5-(C$_{1-2}$ alkyl)-1,2,4- oxadiazol-3-yl, a Z' cyano group may be reacted with hydroxylamine, in a polar solvent such as methanol, to yield the corresponding amide oxime. The amide oxime may be cyclised using a suitable derivative of a C$_{2-3}$ alkanoic acid such as the anhydride or a trialkylorthoacetate such as triethyl orthoacetate, the acid derivative acting as the solvent, at elevated temperature.

When Z represents b 5-(H or C$_{1-2}$ alkyl)-1,3,4 -oxadiazol-2-yl, a Z' carboxy or carboxy ester group may be converted to the acid hydrazide by conventional procedures. For example, the acid may be converted to a C$_{1-6}$ alkyl ester e.g. methyl, with the appropriate C$_{1-6}$ alkanol e.g. methanol under conventional esterification conditions., and the resulting ester reacted with hydrazine at elevated temperature to give the acid hydrazide. The acid hydrazide may then be cyclised by condensation with a suitable derivative of the appropriate C$_{1-3}$ alkanoic acid RCO$_2$H, e.g. a trialkyl orthoester, such as the triethyl ortho-ester, the acid derivative acting as the solvent, at elevated temperature. Alternatively, the ester is treated with an acyl hydrazide at ambient temperature followed by cyclisation with methanesulphonic acid and phosphorus pentoxide.

When Z represents b 5-(H or C$_{1-2}$ alkyl)-1,3,4 -thiadiazol-2-yl a Z' acid hydrazide may be reacted with a suitable acylating agent such as methyl formate or an acetyl or propionyl halide-to give a diacyl hydrazide group, —CONHNHCOR which can be cyclised using phosphorus pentasulphide. The cyclisation is preferably carried out in the absence of solvent with the nitrogen of the azabicycle protected as the hydrochloride salt.

When Z represents 1,3-oxazol-2-yl, the conversion may be effected by reaction of a Z' aminocarbonyl group with vinylene carbonate at elevated temperature in the presence of a strong acid such as polyphosphoric acid, which may also function as the solvent.

When Z represents b 5-(H or C$_{1-2}$ alkyl)-1,3-oxazol-2-yl, a Z' carboxy group may first be converted to the carboxylic acid chloride and then reacted with a compound of formula NH$_2$CH$_2$CR(OR')$_2$, or the Z' carboxy group may be reacted directly with the compound of formula NH$_2$CH$_2$CR(OR')$_2$ in the presence of a condensing such as dicyclohexylcarbodiimide or a chloroformate ester such as ethyl chloroformate, to give a group CONHCH$_2$C(OR')$_2$R; which may be cyclised using a suitable dehydrating agent such as polyphosphoric acid, phosphorus oxychloride, phosphorus pentachloride, sulphuric acid or sulphuryl chloride, preferably polyphosphoric acid.

A Z b 5-(H or C$_{1-2}$alkyl)-1,3-thiazol-2-yl group may be obtained by cyclisation of a Z' —CONHCH$_2$C(OR')$_2$R group using phosphorus pentasulphide. The reaction is preferably carried out in the absence of solvent with the nitrogen of the azabicycle protected as the hydrochloride salt.

1,3-Oxazol-2-yl groups 4-methyl-substituted may be provided by the cyclisation of a Z' aminocarbonyl group with propargyl alcohol or acetate ester thereof, in the presence of a dehydrating agent such as polyphosphoric acid,using a catalyst such as HgSO$_4$, at elevated temperature.

Alternative routes to optionally 4- substituted 1,3-oxazol-2-yl groups include:

i) the condensation of a Z' aminocarbonyl group with the appropriate compound BrCH$_2$COR at elevated temperature; or ii) the reaction of a Z' carboxy group under basic conditions with the appropriate compound BrCH$_2$COR to give a group —COOCH$_2$COR which may be cyclised with ammonium chloride.

Where R is hydrogen the aldehyde is preferably protected as an acetal.

During the reaction (i) above, the nitrogen atom of the azobicyclic moiety may require protection.

When Z is 4-(H or C$_{1-2}$alkyl)-1,3-thiazol-2-yl a Z' aminothiocarbonyl group may be reacted with the appropriate a-halo acyl compound such as BrCH$_2$COCH$_3$ as indicated for the corresponding 1,3-oxazole.

1,3-Oxazol-4-yl groups optionally 2-substituted may be provided by reacting a bromomethylcarbonyl group with an appropriate C$_{1-3}$ alkanoic acid amide. Preferably, the reaction with acetamide is carried out at elevated temperature and the reaction with formamide is carried out in sulphuric acid.

An unsubstituted 1,3-oxazol-4-yl group may alternatively be obtained by treatment of a Z' —CH$_2$N≡C group with a formate ester such as methyl formate after deprotonation with a strong base such as n-butyl lithium or potassium t-butoxide.

When Z represents 3-(H or C$_{1-2}$alkyl)-1,2-oxazol-5-yl, the reaction of a Z' CH$_3$CO group may be carried out at depressed temperature with ethyl formate, acetate or propionate in a suitable solvent such as toluene, under basic conditions such as sodium hydride and catalytic ethanol, followed by reflux, to yield the sodium salt of the resulting dicarbonyl compound. Cyclisation at ambient temperature with an aminating agent such as hydroxylamine-O-sulphonic acid in a dry solvent such as methanol, ethanol or diglyme, preferably in the presence of an acid such as sulphuric acid, p-toluene sulphonic acid or potassium hydrogen sulphate to minimise amination of the azabicycle, yields a compound of formula (I).

Alternatively, the dicarbonyl compound sodium salt may be treated prior to the cyclisation step with dimethylamine in ethanol in the presence of glacial acetic acid at ambient temperature to give the vinylogous amide which may be cyclised as described above.

When Z represents an optionally 5-substituted 1,2-oxazol-3-yl group, a Z' —C≡N$^+$—O$^-$ nitrile oxide group may be reacted with an olefin of the structure R—C(X)=CH$_2$, where X is halo such as chloro, OCOCH$_3$ or OSi(CH$_3$)$_3$. The highly reactive nitrile oxide may conveniently be generated in situ from an appropriate Z' halo oxime —C(Br)=NOH by treatment with a base such as triethylamine in a solvent such as N,N-dimethylformamide. The halo oxime is prepared by treatment of a Z' —CH=NOH oxime group with N-bromosuccinimide in N,N-dimethylformamide at ambient temperature, the azabicyclic being in the form of the hydrochloride salt. The Z' —CH=NOH oxime group may be prepared from a Z' —CHO group by reaction with hydroxylamine hydrochloride in a solvent such as methanol.

When Z represents a 2-(H or methyl)-1,3-oxazol-5-yl group, a Z' —COCH$_2$Br group may be converted to —COCH$_2$NH$_2$ by treatment with NaN$_3$ in acetone or N,N-dimethylformamide followed by treatment by triphenyl phosphine in methanol, or by treatment with hexamethylene tetramine followed by hydrolysis in methanolic HCl.

The —COCH$_2$NH$_2$ group may then be acylated with the appropriate derivative of formic acid such as acetic-formic anhydride or acetic acid such as the anhydride or chloride to yield an acyl amino ketone which can be cyclised using a suitable dehydrating agent such as polyphosphoric acid, sulphuric acid or phosphorous pentachloride at elevated temperature.

Alternatively, a Z' —CHO group may be treated with tosylmethyl isocyanide and anhydrous potassium carbonate in methanol under reflux to afford a Z 1,3-oxazol-5-yl group.

When Z represents 2-furyl, a Z' CHO group may be treated with a reactive derivative of propanal such as the 3-tosyl derivative and in which the carbonyl group is preferably protected as a cyclic acetal (VIII):

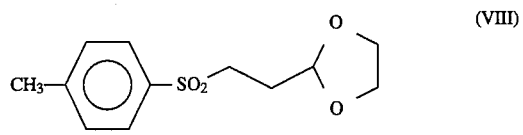

prepared by reaction of sodium 4-methylphenylsulphinate with 2-(2-bromoethyl)-1,3-dioxolane in dimethyl formamide at ambient temperature. The reaction of the compound of formula (VIII) with the Z' —CHO group in an inert solvent such as tetrahydrofuran in the presence of a base such as n-butyl lithium, initially at low temperature, rising to ambient, yields a compound of formula (VIIIa):

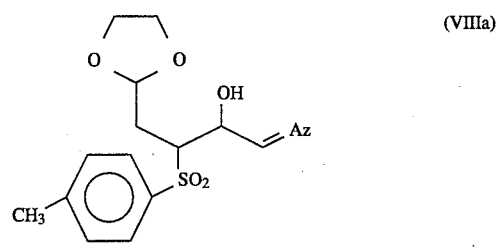

in which A$_Z$ represents the azabicyclic moiety, which may be cyclised at elevated temperature in the presence of an acid such as glacial acetic acid, which may also function as the solvent.

Alkyl-substituted 2-furyl groups may be obtained analogously using the appropriately substituted analogue of the compound of formula (VIII) prepared from the corresponding ketone or aldehyde.

A Z 1,3-thiazol-5-yl group may be obtained by dehydrating and cyclising the corresponding acyl amino ketone using phosphorous pentasulphide at elevated temperature.

Optionally 3-substituted 1,2-thiazol-5-yl groups may be prepared from the corresponding 1,2-oxazolyl group by ring opening effected by treatment with a reducing agent such as Raney nickel and hydrogen in a suitable solvent such as methanol or ethanol to yield a vinylogous amide which may be cyclised using phosphorous pentasulphide in the presence of a suitable oxidising agent such as sulphur or chloranil in a solvent such as toluene at elevated temperature.

Compounds of formula (I)in which Q contains a sulphur atom in place of oxygen may be prepared analogously. A sulphur-containing group Z' is obtained by treatment of a carbonyl-containing group Z' with either phosphorous pentasulphide or with Lawesson's reagent (S. Scheibye, B. S. Pederson and S. O. Lawesson, Bull. Soc. Chim. Belg., 1978, 87(3), 229). The resulting sulphur-containing group Z' may then be converted to the required sulphur-containing group Z analogously to the conversion of carbonyl-containing groups. Where the thiolating agent is phosphorus pentasulphide, this may also effect cyclisation.

Interconversion of carbon substituents R$_1$, R$_2$ and R$_3$ within a group Z may be carried out conventionally. Thus an amino group may be converted to chloro via a diazonium intermediate.

In the above description, R represents H, methyl or ethyl as apporpriate and R' represents C$_{1-6}$ alkyl such as methyl or ethyl or two R' groups together represent C$_{2-6}$ polymethylene such as ethylene.

Compounds of formulae (II) and (III) are known compounds or may be prepared as described in for example EP 0261763.

Intermediates of formula (II) where A' and L$_1$ together represent —COO—, m=O, C is —(CH$_2$)$_2$— and E is —CH$_2$— are described in, for example, Kuthan et al., Coll. Czechoslov. Chem. Comm., 1977, 42, 283 or may be prepared therefrom by conventional hydrogenation of the pyridine ring over 5% Pt/C, and benzylation of the nitrogen atom by treatment with benzyl bromide and potassium carbonate in dry acetone.

The compound of formula (II) where R$_5$ is an N-protecting group, A' and L$_1$ together represent —COO—, m=O, C is —CH$_2$— and E is —(CH$_2$)$_2$— may be prepared by a 1,3-dipolar cycloaddition reaction of a compound of formula (IX):

(IX)

where R$_6$ is an N-protecting group, with 5,6-dihydro-2H-pyran-2-one in the presence of a catalytic amount of trifluoroacetic acid.

Intermediates of formula (II) where L$_1$ is a leaving group are described in, for example, Spry et al., J. Org. Chem., 1969, 34, 3674 and Hasse et al., Chem. Ber., 1960, 93, 1686.

Intermediates of formula (III) are described in, for example, Martell et al., J. Pharm. Sci., 1963, 52(4), 331, Sternbach et al., J. A. C. S., 1952, 74, 2215, Thill et al., J. Org. Chem., 1968, 33, 4376 and EP-0 094 742.

Compounds of formula (III) may be prepared from a compound of formula (X):

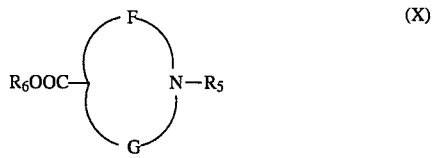
(X)

where R$_6$ is C$_{1-4}$ alkyl and the remaining variables are as previously defined.

Compounds of formula (X) are known compounds or may be prepared by analogous methods to those for preparing known compounds. The compound of formula (X) where F is (CH$_2$)$_2$, G is CH$_2$ and R$_5$ is benzyl may be prepared by the cyclisation of di-C$_{1-4}$ alkyl itaconate in the appropriate alkanol with benzylamine at elevated temperature, followed by reduction of the resulting oxo group at the 2-position of the pyrrolidine ring with BH$_3$ in tetrahydrofuran, at ambient to elevated temperature.

Alternatively, and preferably, a dipolar cycloaddition of a C$_{1-4}$ alkyl acrylate with a compound of formula (IX) in the presence of a catalytic amount of trifluoroacetic acid yields a compound of formula (X) directly.

Compounds of formula (IX) may be prepared conventionally, by the reaction of the primary amine R$_5$NH$_2$ successively with chloromethyltrimethylsilane and formaldehyde followed by methanol and anhydrous potassium carbonate.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The compositions of the invention may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50 mg; and such unit doses may be administered more than once a day, for example two or three times a day, so that the total daily dosage is in the range of about 0.01 to 5 mg/kg; and such therapy may extend for a number of weeks or months.

Within the above indicated dosage ranges no toxicological effects are indicated for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

In another aspect the invention provides the use of a compound of formula (I) or a pharmaceutically acceptable salt thereof for the preparation of a medicament for the treatment and/or prophylaxis of dementia.

The following examples illustrate the invention and the following description illustrates the preparation of intermediates thereto.

DESCRIPTION 1

(±) Z
3-(Ethoxycarbonylmethylene)-1-azabicyclo-[2.2.1]-heptane oxalate salt (D1)

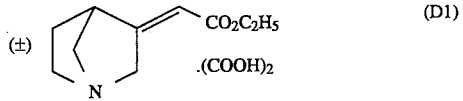

Triethylphosphonoacetate (2.69 g, 0.012 moles) in dry DMF (10 ml) was treated with potassium t-butoxide (1.59 g, 0.013 moles) at 0° C. with continuous stirring under an atmosphere of nitrogen. After 30 minutes (±)1-azabicyclo [2.2.1]heptan-3-one (D6, 1.11 g, 0.01 moles) in DMF (10 ml) was added at 0° C. and the stirred solution allowed to warm to room temperature over a period of 30 min. After standing at room temperature for 1h the reaction was neutralised with acetic acid and concentrated in vacuo to a gum. The gum was then partitioned between aqueous potassium carbonate and chloroform. The chloroform solution was separated and concentrated in vacuo to a gum. Kugelröhr distillation in vacuo afforded a colourless oil b.pt 200° C. at 0.5 mm. The oil was dissolved in ether (20 ml) and treated with oxalic acid (900 mg) in methanol (2 ml). The title compound oxalate salt (D1) slowly crystallised out. Recrystallisation from methanol-ether afforded the pure title compound free from the E isomer as needles (D1) (2.13 g; 78%). m.p. 140°–150° C.

$^1$H NMR (DMSO) δ: 1.30 (3H, t, J=9 Hz, CH$_3$), 1.65–1.75 and 2.25–2.4 (each 1H, m, 5-CH$_2$); 3.25–3.7 (5H, m, 4-CH, 6-CH$_2$, 7-CH$_2$); 4.15–4.25 (2H, q, J=9 Hz, CH$_2$CH$_3$); 4.35 (2H, m, 2-CH$_2$); 6.12 (1H, s, CH=C).

DESCRIPTION 2

(±) E/Z
3-(N-Methyl-N-methoxyaminocarbonylmethylene)-1-azabicyclo[2.2.1]heptane (D2)

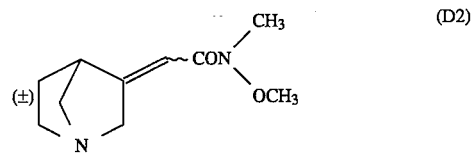

Z/E 3-(Ethoxycarbonylmethylene)-1-azabicyclo[2.2.1]-heptane oxalate salt (prepared as in Description 1 without recrystallisation) (0.5 g, 0.0018 mol) in 5N hydrochloric acid (30 ml) was heated under reflux for 2 h. The solution was then concentrated in vacuo to a gum which was treated with thionyl chloride (10 ml) and dichloromethane (30 ml) under reflux for 30 min until a homogenous solution was obtained. The solution was then concentrated in vacuo to a gum which was azeotroped twice with dry toluene to remove the last traces of thionyl chloride. The acid chloride in dry dichloromethane (20 ml) was treated with O,N-dimethyl hydroxylamine hydrochloride (0.2 g, 0.002 mol) and pyridine (0.8 g, 0.01 mol) at 0° C. with continuous stirring. The reaction was allowed to warm to room temperature overnight and then washed with saturated aqueous potassium carbonate solution. The organic phase was separated, dried (Na$_2$SO$_4$) and concentrated in vacuo to a gum. Kugelröhr distillation in vacuo afforded the title compound D2 (270 mg, 60%) as a colourless oil b.p. 190°–200° C. which contained 15% of the E isomer by NMR.

$^1$H NMR DMSO δ: 1.35–1.5 (1H, m, 6H), 1.8–2.0 (1H, m, 6H), 2.4–2.65 (3H, m), 2.8–2.95 (1H, m), 3.13 (1H, d, J=5 Hz) 3.18 and 3.22 together E/Z (3H, s, N-CH$_3$), 3.6 and 3.75 each (1H, d, m, J=16 Hz, 2-H), 3.68 and 3.72 together E/Z (3H, s, O—CH$_3$), 6.1 (E) and 6.38 (Z) together (1H, s, =CH).

DESCRIPTION 3

(±) E/Z 3-(Ethoxycarbonylmethin )-1-azabicyclo[3.2.1]octane (D3)

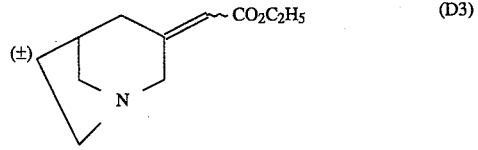

Triethylphosphonoacetate (7.17 g, 0.032 mole) in dry dimethylformamide (20 ml) was treated with potassium tertiary butoxide (3.9 g, 0.035 mole) under an atmosphere of nitrogen for 30 min at 0° C. To this solution was added 1-azabicyclo[3.2.1]octan-3-one* (1.93 g, 0.016 mole) in dry dimethylformamide (30 ml) and the reaction allowed to warm to room temperature over 4 h. The reaction was quenched with acetic acid (5 ml) evaporated to dryness in vacuo and the residue partitioned between saturated aqueous potassium carbonate and chloroform. The organic phase was separated, dried (Na$_2$SO$_4$) and concentrated in vacuo to a yellow oil. The oil was chromatographed on silica in a gradient of 20–40% methanol in chloroform. Elution with 30% methanol in chloroform afforded the title compound (D3) (1.05 g, 34%) as a viscous oil containing a 3:1 mixture of Z/E isomers.

*D. P. Thill and H. S. Aaron, J. Org. Chem., 1968, 33, 4376.

$^1$H NMR (CDCl$_3$) δ: 1.29 (3H, t), 1.57–1.9 (2H, m), 2.2–2.72 (2H, m), 2.72–3.16 (4H, m), 3.2–3.74 (3H, m), 4.15 (2H, q), 5.73 (1H, s). $^{13}$C NMR (CDCl$_3$) (major isomer) δ: 31.3 (CH$_3$), 47.4 (C-6), 52.2 (C-5), 53.1, 69.2, 77.0, 77.1, 80.5, 135.2 (=CH), 173.9 (C=), 182.9 (C=O)

DESCRIPTION 4

(±) 1-Benzyl-3-methoxycarbonylpyrrolidine (D4)

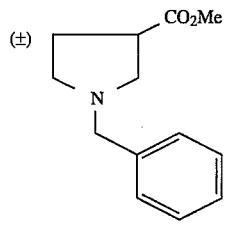

(D4)

Ethyl acrylate (86 g, 1.0 mole) in dichloromethane (2 L) was cooled to 0° C. and treated with N-benzyl-N-(methoxymethyl)-N-[(trimethylsilyl)methyl]amine (compound D17 of EP 0363085) (300 g, 80% pure by $^1$H NMR, 1 mole) with stirring over a period of 10 min whilst maintaining the temperature between −5° C. and 0° C. A solution of trifluoroacetic acid in dichloromethane (100 ml, 1 molar) was added at such a rate that the temperature did not rise above 5° C. and the reaction allowed to warm to room temperature overnight. The solution was then washed with saturated aqueous potassium carbonate solution, dried over sodium sulphate and concentrated in vacuo to a gum. The glum was distilled in vacuo to afford the title compound. (D4) as a single main fraction. Bpt 150°–160° at 8 mm (232 g, 100%).

$^1$H NMR (CDCl$_3$) δ: 2.05–2.15 (2H, m), 2.45–2.75 (3H, m), 2.75–2.85 (1H, t, J=11 Hz), 3.0–3.10 (1H, q, J=11 Hz), 3.60 (2H, s, CH$_2$Ar), 3.7 (3H, s, CH$_3$), 7.2–7.35 (5H, m, Ph)

DESCRIPTION 5

(±) 1-Ethoxycarbonylmethyl-3-methoxycarbonyl pyrrolidine (D5)

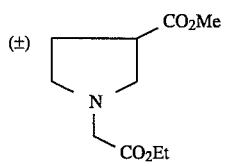

(D5)

(±) 1-Benzyl-3-methoxycarbonyl pyrrolidine (D4) (232 g, 1.05 mole) was dissolved in ethanol (1 L) and treated with ethyl bromoacetate (1.84 g, 1.1 mole) and potassium carbonate (27 g, 0.2 mole) under reflux for 6 h. The reaction was then allowed to cool and was filtered. The filtrate was concentrated in vacuo to an oil which was swirled with ether to remove unreacted ethyl bromoacetate. The oil was separated from the ether and redissolved in ethanol (500 ml) and treated with acetic acid (30 ml). To this was added 10% palladium on charcoal (20 g) and the mixture stirred under an atmosphere of hydrogen until the uptake was complete. The reaction was then filtered through celite and concentrated to a gum. The gum was partitioned between dichloromethane and saturated aqueous potassium carbonate solution. The organic phase was separated dried over sodium sulphate and concentrated to a gum. vacuum distillation afforded the title compound (D5) (132.5 g, 0.62 mole) as the main fraction. B.p. 110–120 at 0.5 mm.

$^1$H NMR (CDCl$_3$) δ: 1.3 (3H, t, J=8 Hz, CH$_3$), 2.1–2.2 (2H, m), 2.5 (1H, q, J=8 Hz), 2.75 (1H, Br S), 2.85–3.0 (1H, m), 2.05–3.2 (2H, m), 3.3 and 3.4 each (1H, d, J=16 Hz), 3.7 (1H, s), 4.2 (2H, q, J=8 Hz)

DESCRIPTION 6

(±) 1-Azabicyclo[2.2.1]heptane-3-one (D6)

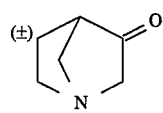

(D6)

Potassium butonide (165 g, 1.35 mole in dry toluene (2 L) was heated to reflux under an atmosphere of nitrogen. 1-Ethoxycarbonylmethyl-3-methoxycarbonyl pyrrolidine (D5) (132 g, 0.62 mole) was added dropwise over a period of 1 h and the reaction was refluxed for a further 2 h. The reaction was then cooled to −10° C. and acetic acid (80 ml) added with continuous stirring. The toluene solution was then repeatedly extracted with 5N hydrochloric acid (4×500 ml) and the combined aqueous extracts heated under reflux for 10 h. The solution was concentrated to 1 L and neutralised by addition of saturated aqueous potassium carbonate solution. Extraction with dichloromethane (5×800 ml) afforded a yellow oil which was distilled in vacuo to afford the title compound (24.9 g, 0,226 mole, 36%). B.p. 80°–82° C. at 0.4 mm which solidified on cooling to give a very hygroscopic solid. M.pt 40°–50° C.

$^1$H NMR (CDCl$_3$) δ: 1.73–1.85 (1H, m), 2.0–2.2 (1H, m), 2.65–2.85 (4H, m), 3.3–3.15 (3H, m)

DESCRIPTION 7

2-(Bromomethyl)-1,3-thiazole (D7)

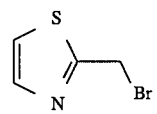

(D7)

2-(Hydroxymethyl)-1,3-thiazole* (4.14 g, 0.036 moles) was dissolved in dry dichloromethane (130 ml) and cooled to 0° C. Triethylamine (5.5 ml, 0.039 moles) was added, followed by dropwise addition of methanesulphonylchloride (3.2 ml, 0.041 moles). After stirring at room temperature for 2 h the reaction mixture was washed with saturated sodium bicarbonate solution (2×150 ml), separated, dried (Na$_2$SO$_4$) and evaporated to dryness. The residue was dissolved in dry tetrahydrofuran (175 ml) and treated with anhydrous lithium bromide (3.5 g, 0.04 moles). The mixture was stirred at room temperature for 20 h and then evaporated to dryness. The residue was partitioned between diethyl ether and saturated sodium bicarbonate solution. The organic layer was separated, dried (Na$_2$SO$_4$) and evaporated to dryness. The residue was distilled under vacuum to give the title compound D7 (3.6 g, 56%) b.p. 82°–86° C. at 7 mmHg.

$^1$H NMR (CDCl$_3$) δ: 4.77 (2H, s), 7.40 (1H, d), 7.74 (1H, d)

*A. Dondoni, G. Fantin, M., Fogagnolo, A. Medici and P. Pedrini, Tetrahedron, 44(7), 2021–2031 (1988).

DESCRIPTION 8

Diethyl (2-thiazolemethyl)phosphonate (D8)

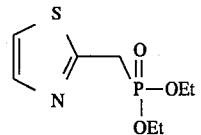

2-(Bromomethyl)-1,3-thiazole (D7) (3.6 g, 0.02 moles) and triethylphosphite (7.2 ml, 0.04 moles) were heated together at 150° C. for 1 h with stirring. The mixture was allowed to cool and the excess triethylphosphite was removed under vacuum. The residue was subjected to column chromatography on silica gel eluting with 0–5% methanol/chloroform. This gave the title compound D8 as an orange oil (2.1 g, 47%).

$^1$H NMR (CDCl$_3$) δ: 1.32 (6H, t), 3.66 (2H, d, J=25 Hz), 4.07–4.21 (4H, m), 7.30 (1H, d), 7.72 (1H, d)

DESCRIPTION 9

3-(Aminocarbonylmethin)-1-azabicyclo[2.2.2]octane (D9)

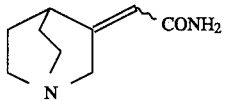

Z-3-(Ethoxycarbonylmethylene)-1-azabicyclo[2.2.2]octane* (2.0 g, 0.10 mol) was stirred with concentrated (0.88) ammonia (50 ml) for 18 days in a sealed flask. Further ammonia (20 ml) was added and the mixture stirred for a further 7 days. The mixture was then saturated with potassium carbonate solid, extracted with EtOAc (5×200 ml), the organic extracts dried (Na$_2$SO$_4$), and evaporated to dryness to yield the title compound D9 as a white solid (1.56 g, 94%).

$^1$H NMR (CDCl$_3$) 1.75 (4H, m), 2.41 (1H, m), 2.92 (4H, m), 4.01 (2H, bs), 5.44 (2H, bs, NH$_2$), 5.61 (1H, m, alkene-H)

*L. N. Yakhontov, L. I. Mastafanova and M. V. Rubstov, Zh. Obstich. Khim., 1963, 33 (10), 3211–14 (C.A. 1964, 4109e)

EXAMPLE 1

(±) Z 3-([3-Amino-1,2,4-oxadiazol-5-yl]methin)-1-azabicyclo[2.2.1]heptane (E1)

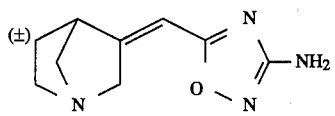

Sodium (600 mg, 0.026 moles) was dissolved in ethanol (30 ml) under an atmosphere of nitrogen. The resulting solution was cooled to room temperature and treated sequentially with powdered 3A molecular sieve (10 g), hydroxy guanidine sulphate sesquihydrate (1.96 g, 0.074 moles) and Z(3-ethoxycarbonylmethylin)-1-azabicyclo[2.2.1]heptane oxalate salt (1g, 0.037 moles) (D1). The stirred reaction mixture was then heated under reflux for 2.5 h. The reaction was then cooled and neutralised by the addition of acetic acid. The solution was then filtered and concentrated in vacuo to a gum. The gum was partitioned between chloroform and saturated aqueous potassium carbonate solution. The organic phase was separated, dried over anhydrous sodium sulphate and concentrated in vacuo to a gum. Crystallisation from acetone afforded the title compound (E1) (190 mg; 26%) as needles. m.p. 184°–187° C.

$^1$H NMR (CD$_3$OD) δ: 1.45–1.55 and 1.95–2.10 (each 1H, m, 5-CH$_2$), 2.55–2.75 (3H, m), 2.87–3.0 (1H, m), 3.3 (1H, s, 4-H), 3.5–3.75 (2H, m, 2-CH$_2$), 6.35 (1H, m, CH=C).

$^{13}$C (CDCl$_3$) δ: 30.9 (C-5), 48.5 (C-4), 53.7, 61.4, and 62.9 (together C-2, 6, 7), 102.7 (—C$\underline{H}$=C), 166.7, 170.5, 175.0 (C-3, 3', 5'). Found: C, 56.2; H, 6.4, N, 28.7% C$_9$H$_{12}$N$_4$O requires: C, 56.2; H, 6.3; N, 29.1%

EXAMPLE 2 AND EXAMPLE 3

(±) Z 3-([3-Methyl-1,2,4-oxadiazol-5-yl]methin)-1-azabicyclo[2.2.1]heptane oxalate salt (E2)

(±) E 3-([3-Methyl-1,2,4-oxadiazol-5-yl]methin)-1-azabicyclo[2.2.1]heptane oxalate salt (E3)

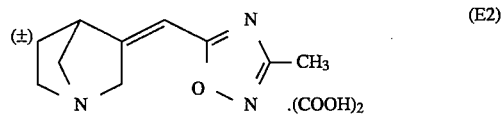

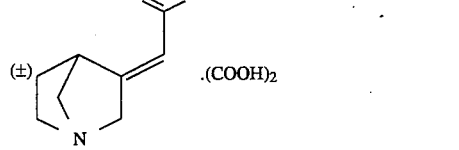

Z/E 3-(Ethoxycarbonylmethin)-1-azabicyclo[2.2.1]heptane oxalate salt (10:1) (prepared as in Description 1 without recrystallisation) (1.5 g, 0.0055 mol) was heated under reflux in concentrated hydrochloric acid (15 ml).and water (7 ml) for 1 h. The reaction was evaporated to dryness and azeotroped once with toluene to afford a pale brown oil. The oil was treated with a mixture of thionyl chloride (16 ml) and dichloromethane (30 ml), and heated under reflux until a homogenous solution persisted. The reaction was then concentrated in vacuo and azeotroped three times with toluene to give the acid chloride as a buff-coloured solid free of thionyl chloride. The solid was taken up in ethanol-free chloroform and treated with acetamide oxime (Compound D17 in EP-0261763) (0.65 g, 1.6 eq) under an atmosphere of nitrogen. The mixture was heated under reflux for 45 min. Saturated aqueous potassium carbonate was added, the organic phase was separated, dried (Na$_2$SO$_4$) and evaporated to afford a brown gum. This oil was heated under reflux in xylene for 9 h. Xylene was removed in vacuo to leave a pale brown oil. This oil was chromatographed on silica in 5% methanol/chloroform to afford the faster running Z isomer followed by the slower running E isomer.

The faster running isomer (200 mg) was crystallized as the oxalate salt and recrystallized from methanol/ether to afford the title compound (E2) as needles (130 mg, 0.463 mmol in 8% yield). m.p. 118° C. The slower running isomer crystallized as the oxalate salt and recrystallized from methanol/acetone to afford the title compound (E3) as needles (23 mg, 0.08 mmol in 1.5% yield). m.p. 174° C.

For Z isomer E2 Oxalate $^1$H NMR (CD$_3$OD) δ: 1.83–1.95 and 2.35–2.5 (each 1H, m, 5CH$_2$), 2.4 (3H, s, CH$_3$), 3.37–3.5 (3H, m), 3.55–3.68 (1H, m), 3.73 (H, d, J=4 Hz), 4.4 and 4.54 (each 1H, d, J=16 Hz, 2CH$_2$), 6.72 (1H, s, 8CH). Oxalate $^{13}$C NMR (CD$_3$OD) δ: 11.4 (CH$_3$, C-9), 28.0 (CH$_2$, C-5), 45.4 (CH, C-4), 52.9, 60.5 and 60.9 (each CH$_2$ and C-2, C-6 or C-7), 105.9 (CH, C8), 153.8 (CH), 168.8 (CH), 174.7 (C-3, C-3', C-5'), 166.6 (oxalate).

For E isomer E3 Oxalate $^1$H NMR (CD$_3$OD) δ: 1.8–1.95 and 2.4–2.55 (each 1H, m, 5CH$_2$), 2.4 (3H, s, CH$_3$), 3.3–3.41 and 3.55–3.6 (each 1H, m, 6CH$_2$), 3.44 (2H, s, 7CH$_2$), 4.1 and 4.33 (each 1H, d, J=16 Hz, 2CH$_2$), 4.6 (1H, d, J=4 Hz, 4CH), 6.5 (1H, s, 8CH).

EXAMPLE 4

(±)E/Z
3-([1,3-Oxazol-5-yl]methin)-1-azabicyclo[2.2.1]heptane oxalate salt (E4)

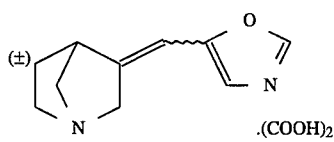
(E4)

E/Z 3-(N-methyl-N-methoxyaminocarbonylmethin)-1-azabicyclo[2.2.1]heptane (D2) (0.25 g, 0.00134 mole) in dry tetrahydrofuran (30 ml) was treated with diisobutyl aluminium hydride in toluene (0,002 mole, 1.33 ml of a 1.5M solution) at –60° C. under an atmosphere of nitrogen. The reaction was then warmed to –20° C. and maintained at this temperature for 1.5 h. The reaction was cooled to –60° C. and poured into 5N hydrochloric acid (25 ml) at –10° C. The reaction was then concentrated in vacuo to a gum and partitioned between chloroform and saturated aqueous potassium carbonate solution. The organic phase was separated, dried (Na$_2$SO$_4$) and concentrated in vacuo to a gum. Chromatography on a short alumina column in 10% methanol in ethyl acetate afforded the aldehyde (0.16 g, 0.0011 mole) as a colourless oil which NMR indicated was a 2:1 mixture of Z/E isomers. The aldehyde (0.15 g, 0.00109 mole) in methanol (10 ml) was treated with para toluene sulphonylmethylisocyanide (TosMIC) (260 mg, 0.0014 mole) and potassium carbonate (0.15 g, 0.00109 mole) under reflux for 1.5 h. The reaction was concentrated in vacuo to a gum. Chromatography on silica in a gradient of 10–30% methanol in chloroform afforded the title compound (E4) as the major fraction (0.157 g, 67%). NMR indicated that this was a 2:1 mixture of Z/E isomers. The oxalate salt crystallised from methanol/ether. m.p. 85°–90° C.

Oxalate $^1$H NMR (CD$_3$OD) δ: 1.8–1.95 (1H, m, 5H), 2.28–2.45 (1H, m, 5H), 3.3–2.7 (5H, m), 4.25 and 4.42 (each 1H, d, m, J=16 Hz, 2-H), 6.37 and 6.62 (together 1H, s, 8-H), 7.12 and 7.17 (together 1H, s, 2'-H), 8.23 (1H, s, 4'-H).

EXAMPLE 5

(±) Z
3-([1,3-Oxazol-2-yl]methin)-1-azabicyclo[2.2.1]heptane (E5)

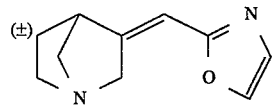

Z/E 3-(Ethoxycarbonylmethin)-1-azabicyclo[2.2.1]heptane oxalate salt (10: 1) (prepared as in Description 1 without recrystallisation) (2 g, 0.007 mole) was dissolved in concentrated hydrochloric acid (15 ml) and water (7 ml) and heated under reflux for 1 h. The reaction was concentrated in vacuo and azeotroped with toluene to give a brown oil. The oil was treated with thionyl chloride (15 ml) and dichloromethane (30 ml) and heated under reflux until a homogenous solution persisted. The reaction was then evaporated to dryness and azeotroped three times with toluene to afford a buff-coloured solid. To a stirred suspension of the solid in dichloromethane (40 ml) at –50° C. under an atmosphere of nitrogen was added a saturated solution of ammonia in dichloromethane (35 ml). The reaction was allowed to warm to room temperature and stir for 45 min. The mixture was partitioned with saturated aqueous potassium carbonate, the organic phase was separated, dried (Na$_2$SO$_4$) and concentrated to afford a buff-coloured solid (1 g, 0.0066 mole, 94% crude yield). To the crude amide (1 g, 0.0066 mole) was added polyphosphoric acid (45 g) and vinylene carbonate (0.75 g, 1.3 eq). The mixture was heated at 120° C. for 2 h. The reaction was allowed to cool slightly and was then cautiously poured into a mixture of saturated aqueous potassium carbonate and ice. The mixture was basified by the addition of solid potassium carbonate and then extracted with ether. The organic phase was separated, dried (Na$_2$SO$_4$) and concentrated in vacuo to afford a yellow oil. The oil was chromatographed on neutral alumina in ethyl acetate. The title compound E5 was isolated as a white crystalline solid (165 mg, 0.0009 mole, 14%). m.p. 73°–76° C.

$^1$H NMR (CDCl$_3$) δ: 1.4–1.55 and 1.84–2.0 (each 1H, m, 5CH$_2$), 2.45–2.73 (3H, m), 2.9–3.03 (1H, m), 3.18 (1H, d, J=5.3 Hz), 3.52 (1H, d, J=16 Hz) and 3.73 (1H, d, J=16 Hz) both (2CH$_2$), 6.35 (1H, t, 8CH), 7.12 (1H, s, oxazole), 7.57 (1H, s, oxazole). $^{13}$C (CDCl$_3$) δ: 30.06 (CH$_2$, C-5), 46.8 (CH, C-4), 53.2 (CH$_2$), 60.7 (CH$_2$) and 61.8 (CH$_2$), (C2, C6 and C7), 104 (CH, C8), 127.0 (CH) and 137.6 (CH) (oxazole C-4'/C-5'), 158.3 and 151.7 (both tertiary C, C-3, C-2').

EXAMPLE 6

(±)E/Z
3-([3-Amino-1,2,4-oxadiazol-5-yl]methin)-1-azabicyclo-[3.2.1]octane (E6)

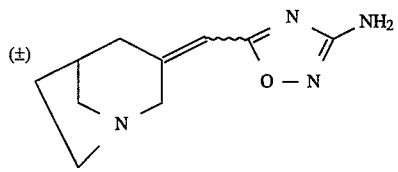

Sodium metal (0.405 g, 0.0176 mole) was dissolved in dry ethanol (40 ml) under an atmosphere of nitrogen, crushed molecular sieve (5 g) was added and the mixture thoroughly stirred. Hydroxyguanidine sulphate hemi hydrate (2.34 g, 0.0176 mole) and E/Z 3-(ethoxycarbonylmethylene)-1-azabicyclo[3.2.1]octane (D3) (0.43 g, 0.0022 moles) were added to the stirred ethoxide solution. The reaction was heated under reflux for 2 h then quenched with acetic acid, filtered and concentrated in vacuo to constant volume. The residue was basified with saturated aqueous potassium carbonate and partitioned with chloroform. The organic phase was separated, dried ($Na_2SO_4$) and evaporated in vacuo to afford a viscous oil. The oil was chromatographed on silica in a gradient of 20–40% methanol in chloroform. Elution with 35% methanol in chloroform afforded title compound (E6) as a white, crystalline solid (160 mg, 0.78 mmoles, 35%) containing a 50:50 mix of E/Z isomers by NMR. m.p. 136°–138° C.

$^1$H NMR (DMSO) for a 1:1 mixture of E/Z isomers δ: 1.45–1.88 (2H, m), 2.28–2.64 (2H, m), 2.64–2.98 (4H, m), 3.09 (1H, t), 3.33–3.5 (1H, m), 3.72 and 4.61 (each 1H, d, J=15.6 Hz together 2CH), 5.38 and 5.44 (1H, each s, $NH_2$), 6.1, 6.12 (1H, each s, olefin CH). $^{13}$C NMR (DMSO) for a 1:1 mixture of E/Z isomers δ: 29.35, 29.77, 34.92, 35.46, 36.51, 42.44, 51.59, 51.88, 57.42, 59.16, 59.42, 63.44, 109.34, 110.12, 154.66, 154.82, 167.93, 167.98, 171.98, 172.16.

EXAMPLE 7

(±) Z
3-([5-Methyl-1,3-oxazol-2-yl]methin)-1-azabicyclo-[2.2.1]heptane oxalate salt (E7)

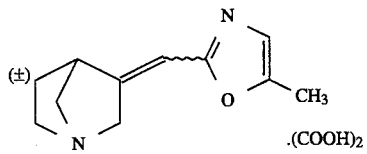

(±)Z/E 3-(Ethoxycarbonylmethin)-1-azabicyclo[2.2.1]-heptane oxalate salt (10.1) (prepared as in Description 1 without recrystallisation) (2.23 g, 0.008 moles) was dissolved in concentrated hydrochloric acid (18 ml) and water (9 ml) and heated under reflux for 1 h. The reaction was concentrated in vacuo and azeotroped with toluene to give a brown oil. The oil was treated with thionyl chloride (18 ml) and dichloromethane (40 ml) and heated under reflux until a homogenous solution was obtained. The reaction was then evaporated to dryness and azeotroped three times with toluene to afford a buff coloured solid. The acid chloride was suspended in dichloromethane (40 ml) and cooled to –40° C. under an atmosphere of nitrogen. To this suspension was added aminoacetone ethylene glycol ketal (1.44 g, 0.012 moles) and pyridine (6 ml). The reaction was allowed to warm to room temperature over 2.5 h with continuous stirring. The solution was then partitioned with saturated aqueous potassium carbonate and the organic phase separated, dried over sodium sulphate and concentrated in vacuo to a gum. To this was added polyphosphoric acid (40 g) and the mixture heated from 120°–160° C. over 30 min and then at 160° C. for a further 30 min. The brown liquid was then poured into a well stirred slurry of ice, excess saturated aqueous potassium carbonate, and ethyl acetate. The organic layer was separated and the aqueous layer extracted with chloroform. The combined organic extracts were concentrated in vacuo to a gum and the ether soluble component chromatographed on alumina in a gradient of 5–20% methanol in ethyl acetate to afford a pale yellow oil (1.67 g) as the main fraction. This oil was taken up in ether and treated with (0.8 g, 0.009 moles) oxalic acid in methanol. The oxalate salt slowly crystallised and this was recrystallised from acetone/ether to afford the title compound (E7) as cubes containing 15% of the E isomer (0.53 g, 0.0019 moles, 24%). m.p. 140°–144° C.

$^1$H NMR of Z isomer (($CD_3$)$_2$SO) δ: 1.68–1.85 (1H, m, 5-H), 2.25–2.45 (1H, m, 5-H), 2.4 (3H, s, $CH_3$), 3.3–3.6 (4H, m, 6-$CH_2$, 7-$CH_2$), 3.7 (1H, d, J=5 Hz, 4-CH), 4.3 and 4.4 each (1H, d, J=16 Hz, 2-CH), 6.6 (1H, s, 8-CH), 7.0 (1H, s, 4'-CH). $^{13}$C NMR of Z isomer (($CD_3$)$_2$SO) δ: 10.5 ($CH_3$), 27.2 ($CH_2$, C-5), 43.2 (CH, C-4), 50.9 ($CH_2$), 58.7 ($CH_2$) and 58.9 ($CH_2$) (C-2, C-6 and C-7), 107.0 (CH, C-8), 124.3 (CH, C-4'), 144.6 (C), 148.6 (C), 158.6 (C) (C-3, C-2', C-5'), 163.5 ($CO_2H$)$_2$.

EXAMPLES 8 AND 9

(±) Z
3-([1,3-Thiazol-2-yl]methin)-1-azabicyclo[2.2.2]octane oxalate salt (E8) and (±) E
3-([1,3-Thiazol-2-yl]methin)-1-azabicyclo[2.2.2]octane oxalate salt (E9)

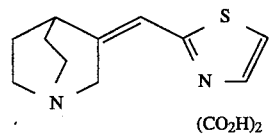

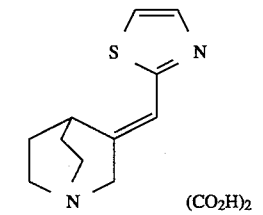

A mixture of (±) 3-([1,3-thiazol-2-yl]hydroxymethyl)-1-azabicyclo[2.2.2]octane (compound D33 of EP 0363085) (0.49 g, 0.0022 moles) and [toluene-4-sulphonic acid monohydrate (1.2 g, 0.0063 moles) was heated under reflux in xylene (60 ml) for 24 h. A 'Dean and Stark' apparatus was used to trap the eliminated water. The mixture was allowed to cool and then concentrated in vacuo. The residue was partitioned between saturated potassium carbonate solution and chloroform. The organic layer was dried (Na2SO4) and evaporated to dryness. The residue was subjected to column chromatography on silica gel eluting with 0–5% methanol/chloroform. This yielded the title compounds as their free bases (E8) (0.23 g, 51%) and (E9) (0.06 g, 13%). The Z isomer (0.085 g, 0.0004 moles) was treated with anhydrous oxalic acid in ethanol/diethyl ether to give the title compound (E8) (0.11 g) m.p. 167°–170° C. The E isomer (0.06 g, 0.0003 moles) was also treated with anhydrous oxalic acid in ethanol/diethyl ether to give the title compound (E9) (0.06 g) m.p. 149°–153° C.

Free base (E8): $^1$H NMR (CDCl$_3$) δ: 1.70–1.92 (4H, m), 2.03–2.11 (1H, m), 2.82–3.09 (4H, m), 3.87 (2H, s), 6.55–6.62 (1H, m), 7.27 (1H, d), 7.79 (1H, d). Free base (E9): $^1$H NMR (CDCl$_3$) δ: 1.70–1.92 (4H, m), 2.82–3.09 (4H, m), 3.60 (2H, s), 3.75–3.80 (1H, m), 6.44 (1H, s), 7.22 (1H, d), 7.75 (1H, d).

EXAMPLES 10 AND 11

(±) Z 3-([1,3-Thiazol-2-yl]methin)-1-azabicyclo[2.2.1]heptane oxalate salt (E10) and (±) E 3-([1,3-Thiazol-2-yl]methin)-1-azabicyclo[2.2.1]heptane oxalate salt (E11)

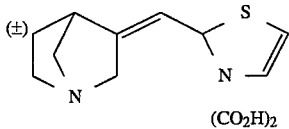
(E10)
(CO$_2$H)$_2$

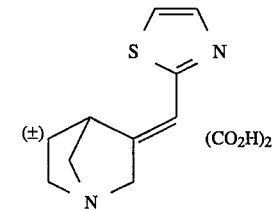
(E11)
(CO$_2$H)$_2$

Diethyl (2-thiazolmethyl) phosphonate (D8) (1.0 g, 0.0045 moles) was dissolved in dry tetrahydrofuran (30 ml) and cooled to 0° C. The mixture was treated with potassium t-butoxide (0.55 g, 0.0045 moles) and stirred for 1 h. (±)1-Azabicyclo[2.2.1]heptan-3-one (D6) (0.5 g, 0.0045 moles) was then added and the mixture stirred for a further 2 h and then evaporated to dryness. The residue was partitioned between chloroform and saturated sodium bicarbonate solution. The organic layer was separated and then extracted with 2N hydrochloric acid (2×50 ml). The aqueous layer was washed several times with chloroform and basified with potassium carbonate followed by re-extraction with chloroform. The organic layer was dried (Na$_2$SO$_4$) and evaporated to dryness. The residue was subjected to column chromatography on silica gel eluting with 0–5% methanol/chloroform. This yielded the title compounds as their free bases (E10) (0.25 g, 29%) and (E11) (0.12 g, 14%). Both compounds were treated with anhydrous oxalic acid in ethanol/diethyl ether to give the Z isomer (E10) (0.28 g) m.p. 160°–164° C. and the E isomer (E11) (0.12 g) m.p. 155°–158° C.

Free base (E10) $^1$H NMR (CDCl$_3$) δ: 1.45–1.60 (1H, m), 1.88–2.00 (1H, m), 2.49–2.76 (3H, m), 2.90–3.08 (1H, m), 3.18–3.22 (1H, m), 3.33–3.42 (1H, m), 3.61–3.71 (1H, m), 6.79 (1H, s), 7.24 (1H, d), 7.76 (1H, d). Free base (E11) $^1$H NMR (CDCl$_3$) δ: 1.45–1.60 (1H, m), 1.90–2.06 (1H, m), 2.50–2.73 (3H, m), 2.91–3.07 (1H, m), 3.12–3.23 (1H, m), 3.48–3.60 (1H, m), 3.93–3.99 (1H, m), 6.42 (1H, s), 7.23 (1H, d), 7.76 (1H, d).

EXAMPLES 12 AND 13

Z 3-([3-Methyl-1,2,4-oxadiazol-5-yl]methin)-1-azabicyclo[2.2.2]octane oxalate salt (E12)

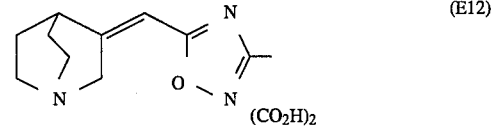
(E12)
(CO$_2$H)$_2$ and E 3-([3-Methyl-1,2,4-oxadiazol-5-yl]methin)-1-azabicyclo[2.2.2]octane oxalate salt (E13)

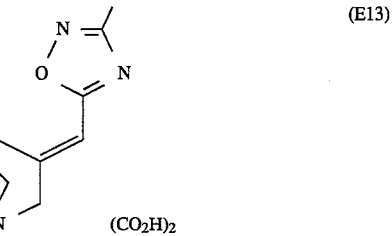
(E13)
(CO$_2$H)$_2$ 3-(Aminocarbonylmethin)-1-azabicyclo[2.2.2]octane (D9) (1.50 g, 9.0 mmoles) and N,N-dimethylacetamide dimethyl acetal (10 ml) were mixed and heated at 120° C. for 1 h. The solution was then concentrated to dryness under reduced pressure and the residue treated with a solution of hydroxylamine hydrochloride (625 mg, 10 mmoles) in 1N aqueous sodium hydroxide (10 ml, 10 mmoles) followed by dioxane (9.7 ml), glacial acetic acid (13.2 ml), and the mixture stirred at room temperature for 30 minutes followed by 1 h at 90° C. The reaction mixture was evaporated to dryness under reduced pressure, dissolved in saturated aqueous potassium carbonate solution and extracted with CHCl$_3$ (3×150 ml). The organic extracts were dried (Na$_2$SO$_4$) filtered and evaporated to dryness under reduced pressure to yield an orange/brown oil which was purified by column chromatography (neutral alumina, eluting with diethylether/ethyl acetate 20–100%). The compound first eluted from the column was the free base of (E12) (360 mg, 20%) and the compound subsequently eluted was the free base of (E13) (138 mg, 7.5%) which contained 15% (E12) as impurity. Both compounds were purified as the oxalate salts.

E12 oxalate salt m.p. 157°–160° C. $^1$H NMR (d$_6$DMSO) 1.87 (2H, m), 2.07 (2H, m), 2.37 (3H, s, CH$_3$), 2.97 (1H, t), 3.30 (4H, bm), 4.39 (2H, s), 6.68 (1H, t, alkene-H) $^{13}$C NMR (D$_6$DMSO) 11.2 (CH$_3$), 22.8 (CH$_2$), 30.8 (CH), 45.5 (CH$_2$), 53.6 (CH$_2$), 105.5 (CH), 153.8 (quart-C), 164.5 (oxalate), 167.1 (quart-C), 172.9 (quart-C) MS found 205.1220 C$_{11}$H$_{15}$N$_3$O requires 205.1215 Analysis C$_{13}$H$_{17}$N$_3$O$_5$ requires C: 52.88; H: 5.80; N: 14.23% found C: 53.06; H: 6.09; N: 14.37%

E13 oxalate salt m.p. 135°–139° C. $^1$H NMR (d$_6$DMSO) 1.81 (2H, m), 2.05 (2H, m), 2.38 (3H, s, CH$_3$), 2.48 (1H, m), 3.25 (4H, m), 4.09 (2H, s), 6.53 (1H, t, alkene-H). $^{13}$C NMR (d$_6$DMSO) 11.2 (CH$_3$), 22.4 (CH$_2$), 25.7 (CH), 45.7 (CH$_2$), 53.5 (CH$_2$), 105.3 (CH), 154.7 (quart-C), 164.4 (oxalate), 167.0 (quart-C), 173.1 (quart-C). MS found 205.1214 C$_{11}$H$_{15}$N$_3$O requires 205.1215

Biological Activity

Radio ligand Binding

Cerebral cortex from Hooded Lister rats (01ac, UK) is homogenised in 2.5 vols ice-cold 50 mM tris buffer pH 7.7 (at 25° C.). After centrifugation at 25,000×g at 4° C. for 15 min the pellet is resuspended in 2.5 vols buffer and the wash repeated 3 times more. The final resuspension is in 2.5 volumes and the homogenates are stored in 1 ml aliquots at −20° C.

Incubations (total volume 2 ml) are prepared using the above buffer with the addition of 2 mM magnesium chloride in the 3H-Oxotremorine-M (3H—OXO—M) experiments. For 3H-Quinuclidinyl Benzilate (3H-QNB), 1 ml of stored membranes is diluted to 30 ml and 0.1 ml mixed with test compound and 0.27 nM (c. 25,000 cpm) 3H-QNB (Amersham International). For 3H—OXO—M, 1 ml of membranes is diluted to 6 ml and 0.1 ml mixed with test compound and 2 nM (c. 250,000 cpm) 3H—OXO—M (New England Nuclear).

Non-specific-binding of 3H-QNB is defined using 1 μM Atropine sulphate (2 μM Atropine) and of 3H—OXO—M using 10 μM Oxotremorine. Non-specific binding values typically are 5% and 25% of total binding, respectively. Incubations are carried out at 37° C. for 30 min and the samples filtered using whatman GF/B filters. (In the 3H—OXO—M experiments the filters are presoaked for 30 min in 0.05% polyethylenimine in water). Filters are washed with 3×4 ml ice-cold buffer. Radioactivity is assessed using a Packard BPLD scintillation counter, 3 ml Pico-Fluor 30 (Packard) as scintillant.

This test provides an indication of the muscarinic binding activity of the test compound. The results are obtained as $IC_{50}$ values (i.e. the concentration which inhibits binding of the ligand by 50%) for the displacement of the muscarinic agonist 3H—OXO—M and the muscarinic antagonist 3H-QNB. The ratio $IC_{50}$(3H-QNB)/$IC_{50}$(3H—OXO—M) gives an indication of the agonist character of the compound. Agonists typically exhibit a large ratio; antagonists typically exhibit a ratio near to unity.

The results are shown in Table 1.

TABLE 1

| Example | [³H-OXO-M $IC_{50}$ (nm) | ³H-QNB $IC_{50}$ (nM) |
|---|---|---|
| E1 | 11.8 | 3,200 |
| E2 | 30 | 1,900 |
| E4 | 294 | 27,930 |
| E5 | 8.6 | 1,800 |
| E6 | 520 | 5,700 |
| E8 | 160 | 1,600 |
| E10 | 165 | 2,500 |

We claim:

1. A pharmaceutical composition which comprises a compound of formula (I) or a pharmaceutically acceptable salt thereof:

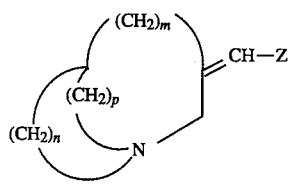

in which either p is 1 and m is 0 and n is 2, or p is 2 and m is 0 and n is 2, and Z is

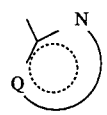

1,2,4-oxadizol-5-yl, 1,3-oxazole-2-yl, or 1,3-thiazole-2-yl wherein any ring carbon atom is optionally substituted by a group $R_1$, or Z is 1,3-oxazole-5-yl in which the 2-position is optionally substituted by $R_2$, and $R_1$ and $R_2$ are independently selected from hydrogen, halogen, $N(R_4)_2$, $C_{2-3}$ alkenyl, $C_{2-3}$ alkynyl, or $C_{1-2}$ alkyl optionally substituted with one, two, or three fluorine atoms, in which $R_4$ is hydrogen or methyl, and a pharmaceutically acceptable carrier.

2. A compound of formula (I) as defined in claim 1 or a pharmaceutically acceptable salt thereof excluding Z 3-([1,3-thiazol-2-yl]methin)-1-azabicyclo[2.2.2] octane.

3. A compound according to claim 2 in which p is 1.

4. A compound according to claim 3 in which [p,n,m] is [1,2,0].

5. A compound according to claim 2 in which Z is 3-amino-1,2,4-oxadiazol-5-yl, 3-methyl-1,2,4-oxadiazol-5-yl, 1,3-oxazol-2-yl, 1,3-thiazol-2-yl, 5-methyl-1,3-oxazol-2-yl and 1,3-oxazol-5-yl.

6. A compound according to claim 2 which is in the Z configuration.

7. (±) Z 3-([3-Amino-1,2,4-oxadiazol-5-yl]methin)-1-azabicyclo[2.2.1]heptane, (±) Z 3-([3-methyl-1,2,4-oxadiazol-5-yl]methin)-1-azabicyclo[2.2.1]heptane, (±) E 3-([3-methyl-1,2,4-oxadiazol-5-yl]methin)-1-azabicyclo[2.2.1]heptane, (±) E/Z 3-([1,3-oxazol-5-yl]methin)-1-azabicyclo[2.2.1]heptane, (±) Z 3-([1,3-oxazol-2-yl]methin)-1-azabicyclo[2.2.1]heptane, (±) Z 3-([5-methyl-1,3-oxazol-2-yl]methin)-1-azabicyclo[2.2.1]heptane, (±) Z 3-([1,3-thiazol-2-yl]methin)-1-azabicyclo[2.2.1]heptane, (±) E 3-([1,3-thiazol-2-yl]methin)-1-azabicyclo[2.2.1]heptane, Z 3-([3-methyl-1,2,4-oxadiazol-5-yl]methin)-1-azabicyclo[2.2.2]octane, or E 3-([3-methyl-1,2,4-oxadiazol-5-yl]methylene)-1-azabicyclo[2.2.2]octane, or a pharmaceutically acceptable salt of any of the foregoing compounds.

8. (±) Z 3-([1,3-Thiazol-2-yl]methin)-1-azabicyclo[2.2.2] octane oxalate salt or (±) E 3-([1,3-thiazol-2-yl]methylene)-1-azabicyclo[2.2.2] octane oxalate salt.

9. A method of treatment and/or prophylaxis of dementia in mammals including humans, which comprises administering to the sufferer an effective amount of a compound of formula (I) as defined in claim 1 or a pharmaceutically acceptable salt thereof.

* * * * *

UNITED STATES PATENT AND TRADEMARK OFFICE
CERTIFICATE OF CORRECTION

PATENT NO. : 5,470,859
DATED : 28 NOvember 1995
INVENTOR(S) : Harry J. Wadsworth et al.

It is certified that error appears in the above-indentified patent and that said Letters Patent is hereby corrected as shown below:

Title page, col. 2,
    In the Abstract, line 1, replace "to" with --for--.

Col. 26,
    In claim 1, line 5, delete the partial formula in its entirety.

Col. 26,
    In claim 8, line 53, replace "methylene" with --methin--.

Signed and Sealed this

Second Day of July, 1996

Attest:

BRUCE LEHMAN

*Attesting Officer*      *Commissioner of Patents and Trademarks*